United States Patent [19]

Widlund et al.

[11] Patent Number: 4,634,440
[45] Date of Patent: Jan. 6, 1987

[54] ABSORBENT ARTICLE

[75] Inventors: Leif U. R. Widlund; Sven G. Bergdahl, both of Mölnlycke, Sweden

[73] Assignee: Molnlycke AB, Goteberg, Sweden

[21] Appl. No.: 733,779

[22] Filed: May 14, 1985

[30] Foreign Application Priority Data

May 15, 1984 [SE] Sweden ............... 8402613

[51] Int. Cl.⁴ ............... A61F 13/16
[52] U.S. Cl. ............... 604/383; 604/385 R
[58] Field of Search ............ 604/358, 369, 378, 380, 604/382, 383, 385

[56] References Cited

U.S. PATENT DOCUMENTS 3,814,191  6/1974  Tilbury .
3,929,135 12/1975  Thompson .
4,041,951  8/1977  Sanford .
4,341,217  7/1982  Ferguson et al. .
4,360,021 11/1982  Stima ............... 604/904 X

FOREIGN PATENT DOCUMENTS 2837072  3/1979  Fed. Rep. of Germany .

Primary Examiner—John D. Yasko
Attorney, Agent, or Firm—Young & Thompson

[57] ABSTRACT

An absorbent article, such as a diaper, a sanitary towel or bandage, having an absorbent core, a liquid-permeable topsheet intended to be in contact with the wearer when the article is worn, and a liquid-impermeable layer arranged on the opposite side of the absorbent core. The liquid-permeable topsheet comprises a perforated but otherwise liquid-impermeable layer, the perforations comprising straight ducts which are of uniform width along the whole of their lengths. The ends of these ducts freely project away from the topsheet and extend into the absorbent core. Fibers extend into the ducts in a manner such that the fiber density in the ducts decreases in a direction away from the free ends of the ducts, so that the fibers form capillaries which taper toward the interior of the absorbent article.

6 Claims, 5 Drawing Figures

ABSORBENT ARTICLE

The present invention relates to absorbent articles, such as disposable diapers, sanitary towels or bandages, of the kind comprising an absorbent core, a liquid-permeable upper layer which is in contact with the wearer in use, and a liquid-impermeable layer located on the opposite side of the absorbent core.

It is extremely important with this kind of absorption product that the upper layer which faces the wearer remains dry, even after having been used for some time, said upper layer being hereinafter referred to as the topsheet.

One serious disadvantage with the majority of known products of this kind is that the skin becomes macerated with prolonged contact with absorbed fluids, for example urine.

In order to solve this problem, it is usual in such known products to form the topsheet thereof from a hydrophobic material, the aim being to draw the moisture away from the skin and into the absorption body by suction. In practice, however, it is found that when the absorption body is pressed against the wearer, previously absorbed fluid will penetrate the thin hydrophobic layer and moisten the skin of the wearer.

Good insulation between the skin of the wearer and an absorption body can be obtained with a relatively thick loosely bound fibre layer which will not conduct fluid, but only permits it to pass. The fluid will thus "fall" straight through the layer into the absorbent element. Insulating layers of this kind, however, create manufacturing problems. For example, the loose fibre layer must be "bound" beneath a topsheet of the absorption body.

Efforts have also been made to create liquid insulation or isolation between the skin of the wearer and the absorption body itself, by using a hydrophobic non-woven layer which is enlarged by embossment. Such an absorption body is described in U.S. Pat. No. 4,041,951. The non-woven layer of the absorbent body there described comprises a large number of downwardly protruding bead-like formations which rest against the planar surface of the absorption body, while areas of the non-woven layer which are not depressed when the body is in use contact the skin of the wearer. The purpose herewith is to impart to the topsheet of the absorbent body sufficient strength to hold the wet absorption body away from the skin of the wearer, even when the absorbent body is subjected to relatively high compression forces. One disadvantage with a topsheet of this kind is that it is too stiff and thus creates discomfort.

U.S. Pat. No. 3,814,101 describes an absorbent article in which the topsheet comprises a liquid-impermeable plastics film in which there are provided a plurality of slots. The sheet also has formed therein a plurality of depressed areas. During the formation of these depressions, the material located therein and the material located therebetween becomes stretched, thereby to open the slots and permit liquid to pass therethrough. The intention herewith is that when saturated with liquid, the absorbent body expands or swells in a manner to press back the depressed areas and in so doing close the slots. One disadvantage with this product, however, is that in order to achieve a satisfactory throughflow of liquid, the plastics sheet must be slotted in a particular manner and that as a result thereof the sheet becomes brittle and is unable to withstand the wear placed thereupon. One of the reasons for using a plastics sheet instead of a fibrous layer is to provide a stronger topsheet, this purpose being defeated when the sheet is slotted. Another inherent disadvantage with an absorbent body produced in accordance with the latter U.S. patent is that there is a grave risk of body fluids being unable to pass through the slots and into the absorbent body, and leaking through the sides instead.

U.S. Pat. No. 3,929,135 describes a plastics film comprising conical capillaries which allow the free transfer of body fluids from the wearer to the absorbent body, while inhibiting at the same time a reverse flow of these fluids. This plastics film affords a much drier surface in contact with the wearer than has been previously obtainable, and has signified a breakthrough in respect of the use of a plastics sheet as the topsheet of absorbent articles of the kind in question. The narrower parts of the conical capillaries are turned towards the absorbent body, causing fluid located on the outside of the film to be drawn rapidly into the absorbent body by suction, thereby inhibiting the transport of fluid in a reverse direction in a relatively efficient fashion.

One disadvantage with plastics films which comprise conical capillaries is that the capillaries tend to collapse when the absorbent article is compressed. The more pointed the conical capillaries the greater the risk of the capillary walls bending and blocking the openings. Thus, the danger with plastics films which comprise conical capillaries is that the holes will become blocked when compressing the absorbent body in use, which can result in body fluid flowing outside the plastics sheet and seeping from the sides thereof.

The object of the present invention is therefore to provide a plastics film with throughpassing capillaries for use with absorbent products of the aforementioned kind, with which the disadvantages inherent with known plastics film of this kind are fully overcome.

Accordingly, an absorbent article produced in accordance with the invention is mainly characterized in that the liquid-permeable topsheet comprises a perforated but otherwise liquid-impermeable layer of material; and in that the perforations consist of straight ducts which have uniform width throughout the whole of their respective lengths and which have ends which project freely from said topsheet and extend into the core of said absorbent product.

Distinct from the teachings of U.S. Pat. No. 3,929,135, the product produced in accordance with the present invention have ducts with straight defining walls. In practice, such straight ducts have been found to resist collapse much more effectively than conical ducts, when a force is applied in the direction of the longitudinal axis thereof. The length of the ducts, i.e. the isolating or insulating distance between the upper layer or topsheet in contact with the wearer and the surface of the actual absorption body at the free ends of the ducts, can also be increased considerably in comparison with a cone. Consequently, with regard to the risk of rewetting the outside of the topsheet, the length of the ducts can be made to compensate the suction effect achieved with conical ducts in drawing body fluid into the absorption body.

In accordance with one suitable embodiment of the invention, fibres may extend into the capillaries in a manner to reduce the fibre density therein in a direction away from the free ends of the ducts, such that the fibres form capillaries which taper towards the interior of the absorbent article. As a result hereof, there is obtained a suction force which acts towards the absorbent core of the article, without the use of conical ducts.

The invention will now be described in more detail with reference to the accompanying drawing, which illustrates mutually different embodiments of the invention. In the drawing, FIG. 1 is a plan view of a sanitary towel provided with a topsheet according to the invention;

Figure 1:
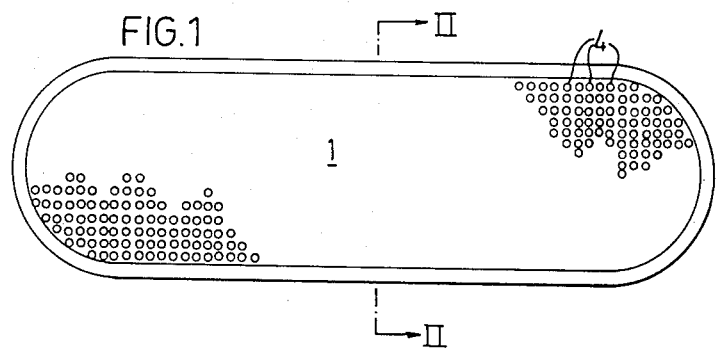
Figure 2:
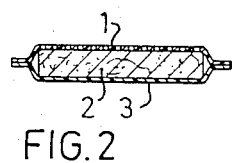
FIG. 2 is a sectional view, taken on the line II—II in FIG. 1.
Figure 3:
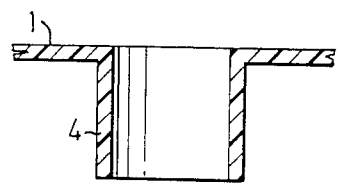
FIG. 3 is a longitudinal sectional view in larger scale of one of the ducts in the topsheet or upper layer of the illustrated sanitary towel.

The sanitary towel illustrated in FIGS. 1 and 2 comprises substantially a plastics film 1, which is made permeable to liquid by the provision of perforations 4 and which forms the upper layer or topsheet of the towel; an absorption core or body 2 and a liquid-impervious plastics film 3, which forms the under layer or bottomsheet of said towel. The two plastics layers 1, 3 are joined together around the edges of the absorption core. The appearance of the holes 4 forming the perforations in the plastics film 1 is shown in FIG. 3, from which it will be seen that said holes are arranged to act as ducts which lead liquid from the topsheet 1 into the absorbent core 2. In accordance with the invention, the holes are of straight cylindrical configuration, which means that the defining walls thereof are able to withstand relatively high axial loads. The total or specific surface area of the holes 4 in the plane of the topsheet is of the order of 10–70% of the surface area of said topsheet. The hole density is such that the defining walls of said holes in the plastics topsheet are together capable of withstanding a relatively large load. In addition hereto, in the case of normal compressive loads occuring when the towel is worn, the hole-defining walls also provide a satisfactory isolating distance between the outersurface of the topsheet and the wet absorbent core located inwardly thereof.

Figure 4:
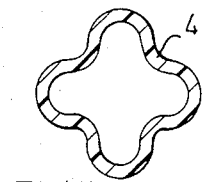
FIG. 4 is a cross-sectional view of a duct according to a modified embodiment.

The bearing capacity of the hole-defining walls can be increased, by giving said walls the undulating cross-sectional shape illustrated in FIG. 4.

The topsheet or upper plastics layer 1 of the sanitary towel illustrated in FIGS. 1 and 2, however, is provided with straight ducts 4, which per se can be formed in a number of mutually different ways.

One method is to use a punch wheel provided with heatable pins having a shape which conforms to that of the straight and narrow capillary ducts required, the liquid-impermeable plastics film 1 being fed in between the punch wheel and a resilient undersurface.

Another suitable method of perforating the topsheet 1 is one in which the liquid-impermeable plastics film is vacuum-formed over a suitable forming means.

The topsheet 1 may also be cast in a mould suitable herefor.

Subsequent to producing the plastics topsheet 1 together with ducts 4 in accordance with one of the aforesaid three methods, it may be necessary to remove such surplus material as flashings, burrs etc. from the ends of the capillary ducts projecting freely from the plastics topsheet 1. This can be readily effected by abrasion, or by heating said ends so as to remove or melt away all unnecessary plastics material liable to block the capillaries.

Figure 5:
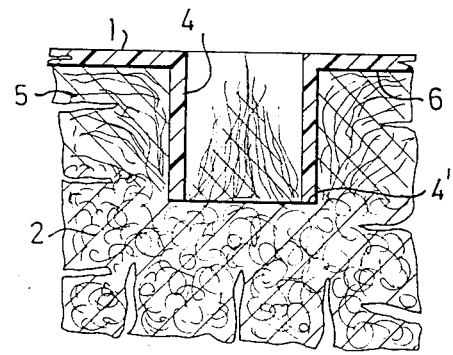
FIG. 5 shows the duct of FIG. 3 in contact with the absorption core of the sanitary towel.

The manner in which the ducts 4 illustrated in FIG. 4 co-act with the absorbent core 2, is illustrated in FIG. 5. Arranged between the core 2 and the perforated plastics topsheet 1 is a thin fibre-layer 5. The fibre layer is airlaid against the plastics layer 1, while applying a partial vacuum with the aid of a suction box or the like, in a manner to draw the fibres into the ducts 4. Prior to airlaying the fibre-layer 5, a thin layer of adhesive is suitably sprayed onto the inner surface 6 of the plastics layer 1, so as to bond the fibres to said surface.

As beforementioned, when the fibres are laid in the aforedescribed manner they are drawn by suction into the ducts 4, and as a result of the applied airlaying procedure the fibre density in said ducts will decrease in a direction away from respective free ends 4 of the ducts. Consequently, those fibres located in respective ducts will create capillaries which taper towards the interior of the absorbent core 2.

In practice, the fibres located in the ducts 4 act as wicks and are operative in drawing liquid present on the outer surface of the topsheet 1 into the absorbent core 2, while at the same time effectively preventing liquid from flowing in the opposite direction, such reverse flow being known as rewetting.

The fibre-layer 5 may either comprise fibres which are particularly suited to the purpose intended, or may comprise the same kind of fibre as that from which the absorbent core 2 itself is made.

The invention is not restricted to the described and illustrated embodiment, which can be modified within the scope of the following claims.

For example, instead of being formed from plastics film, the topsheet or upper layer may comprise a hydrophobized, perforated non-woven material.

We claim:

1. An absorbent article, such as a diaper, a sanitary towel or bandage, having an absorbent core, a liquid-permeable topsheet intended to be in contact with the wearer when the article is worn, and a liquid-impermeable layer arranged on the opposite side of the absorbent core, the liquid-permeable topsheet comprising a perforated but otherwise liquid-impermeable layer; the perforations comprising straight ducts which are of a uniform width along the whole of their lengths, the ends of said ducts freely projecting away from the topsheet and extending into the absorbent core, and fibers extending into the ducts in a manner such that the fiber density in said ducts decreases in a direction away from the free ends of said ducts, such that said fibers form capillaries which taper toward the interior of the absorbent article.

2. An article according to claim 1, in which the fibers extending into the ducts comprise fibers located in a thin fiber layer airlaid on the undersurface of the perforated topsheet.

3. An article according to claim 2, in which the thin fiber layer is bonded to the undersurface of the perforated topsheet and in the ducts by means of a binder.

4. An article according to claim 1, in which the cross-sectional size of the ducts is between 0.1 and 6 mm and the length thereof between 0.2 and 10 mm.

5. An article according to claim 1 in which the walls defining said ducts are of undulating configuration, with their crests and valleys extending in the longitudinal direction of the ducts.

6. An article according to claim 1, in which together the perforations constitute between 10 and 70% of the area of the topsheet.

* * * * *